US006455075B1

(12) United States Patent
Larose

(10) Patent No.: US 6,455,075 B1
(45) Date of Patent: Sep. 24, 2002

(54) METHOD FOR CONTROL OF INSECTS ON PLANTS AND PLANT TISSUE

(76) Inventor: Rene N. Larose, 69 Butler Dr., Glastonbury, CT (US) 06033

(*) Notice: Subject to any disclaimer, the term of this patent is extended or adjusted under 35 U.S.C. 154(b) by 0 days.

(21) Appl. No.: 09/005,661

(22) Filed: Jan. 12, 1998

Related U.S. Application Data

(63) Continuation-in-part of application No. 08/581,863, filed on Jan. 2, 1996, now Pat. No. 5,723,406.
(51) Int. Cl.[7] .................. A01N 59/00; A01N 59/26; A01N 37/02
(52) U.S. Cl. .................. 424/616; 424/601; 424/605; 514/557; 504/114
(58) Field of Search ................. 424/601, 605; 514/557; 504/114

(56) References Cited

U.S. PATENT DOCUMENTS

| | | | |
|---|---|---|---|
| 4,051,059 A | | 9/1977 | Bowing et al. |
| 5,168,655 A | | 12/1992 | Davidson et al. |
| 5,723,406 A | * | 3/1998 | Larose et al. ............ 424/605 |
| 5,998,475 A | * | 12/1999 | James et al. ............ 514/556 |
| 6,197,784 B1 | * | 3/2001 | Fuchs et al. ............ 514/307 |

FOREIGN PATENT DOCUMENTS

| | | | |
|---|---|---|---|
| DE | 3003875 | | 8/1981 |
| DE | 239109 | * | 9/1986 |
| JP | 57-54106 | | 3/1982 |

OTHER PUBLICATIONS

Database WPIDS on STN Online, London: Derwent Publications Ltd., AN 87–014984, DD 239109 A (Veg Gartenbau) Sep. 17, 1986, abstract.

Database WPIDS on STN Online, London: Derwent Publications Ltd., AN 88–304867, JP 63–225, 593 A (Nippon Peroxide Co.) Ltd.) Sep. 20, 1988, abstract.

Gill, Stanton A., "Bathing Thrips: Five Pesticides put to the Test," Grower Talks, vol. 62, No. 8, pp. 46–48, Oct. 1998.*

Felton, Gary W. et al., "Protective Action of Midgut Catalase in Lepidopteron Larvae Against Oxidative Plant Defenses," Journal of Chemical Ecology, vol. 17, No. 9, pp. 1715–1731, 1991.*

* cited by examiner

*Primary Examiner*—John Pak
(74) *Attorney, Agent, or Firm*—Robert S. Smith

(57) ABSTRACT

A method for control of insects on plant tissue which includes applying a solution tht includes hydrogen peroxide to the plant tissue. The hydrogen peroxide solution has a concentration of between 0.05 to 3.00%. In some cases the hydrogen peroxide solution has a concentration of between 0.05 and 1.5%. Some forms of the invention may utilize a hydrogen peroxide solution that further includes an acid selected from the group consisting of acetic acid and phosphoric acid. Various structures are used for applying the hydrogen peroxide solution such as hydraulic spraying, misting, fogging, or injecting the hydrogen peroxide into a commercial cooling system. In some cases the hydrogen peroxide solution is applied to the plant tissue at a variety of stages in the plant production cycle. Other application of the invention include applying misting the hydrogen peroxide solution over terminal stem cuttings until they reach root sufficiency.

20 Claims, No Drawings

METHOD FOR CONTROL OF INSECTS ON PLANTS AND PLANT TISSUE

This application is a continuation-in-part application of application Ser. No. 08/581,863 and filed Jan. 2, 1996 which matured into U.S. Pat. No. 5,723,406. This application disclosed a process both for control of plant tissue infectious diseases are more specifically control of viruses, bacteria, fungi, lower plant forms such as algae, or insects. Most often disease control involves the integrated use of several methods and compounds. Rarely is disease control achieved by a single procedure. The five fundamental principles of disease control are:

1. Exclusion: Preventing pathogens from entering and becoming established in uninfected gardens, fields and greenhouses.
2. Eradication: Elimination of the pathogens once they have become established on plants.
3. Protection: Interposition of a protective barrier between the susceptible host and the pathogen, usually by protective sprays.
4. Resistance: The development and use of genetic mutation.
5. Therapy: The treatment of plants with something that will inactivate or inhibit the pathogen.

BACKGROUND OF THE INVENTION

The invention relates to the horticultural and agricultural field and more particularly to methods for killing, controlling or otherwise impacting the life cycle of insect pests found on agricultural and horticultural products. The term "agricultural and horticultural products" as used herein refers to (1) plants that are raised for their esthetic appearance as well as (2) plants and parts of plants that are cultivated or raised for food including the fruits or any part of such plants both before and after separation from the rest of the plant in addition to (3) the plants and parts of plants that grow wild. Thus, the invention has application to all plants, all fruits that are grown on plants, all cut flowers, or any part of a plant although the invention is not limited to controlling insects on these products.

Pesticides are an important component to agricultural production throughout the world. Pest control pertains to a wide range of environmental interventions that have their objective to kill or reduce to acceptable level insect pests, plant pathogens and weed populations. Specific control techniques include chemical, physical and biological control mechanisms. It has been estimated that pest annually destroy about 35% of all food crops before they are harvested and another 10–20% loss is incurred after the food is harvested.

Chemical controls include chemical agent pesticides that include herbicides, for the control of weeds, insecticides for the control of insect pests and fungicides for the control of soil and plant pathogens that include bacteria, fungi and viruses. Herbicides account for over half of the pesticides that are uses world wide, with 30–35% of pesticide production in the form of insecticides and the balance for the production of fungicides.

It is important to control populations of insects that affect ornamental and agricultural crops and inflict major damage to the crops resulting in crop loss. Insects can either directly affect crop loss by either feeding on the crop itself, they either damaging the plant from producing a fruit or tuber, such as a potato plant or indirectly by either sucking the juices out of a plant that directly affects the aesthetics of the plant, which in the case of ornamental crops such as cut flowers and house plants make the crop unsaleable.

Insects are also a major cause of the spread of infectious disease from plant to plant. As insects feed on the flowers and leaves of the plant, they pick up and transmit potentially deadly pathogenic disease organisms such as bacteria and fungi that are then transmitted to another plant when the insect either crawls on the plant, deposits feces or eats portions of the plant.

Most modern day insecticides are comprised of long lasting, synthetic compounds that affect the nervous system of insects on contact. Among the most effective are the chlorinated hydrocarbons, such as chlordane, and toxaphene and other organophoshates that include malathion, parathion, and dimethoate.

While these pesticides have prove to be very effective at controlling insect pests they have also contributed to an unacceptable environmental cycle that directly affects human health and welfare as well as direct and indirect environmental damage. Modem day insecticides primarily work by placing a poison or toxin residue on the surface of plant tissue or by directly spraying the insect pest with the poison compound.

With a typical insecticide the insect comes into contact with the toxic substance by either being directly sprayed or landing on the residue that has been placed on the plants surface or in the soil in which the plant is ground. The toxin is then either ingested, or enters the insects body through its pores. The toxin then either interferes with the insect's nervous system or other bodily functions such as making it sterile or incapable of eating. Eventually, the insect dies, if the toxin is not deadly enough to produce an immediate kill.

There are several problems that arise from using chemical insecticides. They include resistance, human toxicity, and environment damage.

Since traditional insecticides work on the principal of chemical toxicity, the insect is capable through genetic mutation of developing a resistance to the toxins that affect it. In the insect world, where generations are produced in the pans of weeks, the problem of genetic resistance is common. Within a very short amount of time, many insects that were formally susceptible to certain chemical compounds, find that sometimes within the span of a few years, the chemical either does not produce a kill or the dosage must be increased to produce a kill.

This is why insecticide applicators must cycle their applications of different chemical compounds so as not to allow insects they are trying to control to become accustom to any one chemical compound and ultimately to become immune to the chemical. This practice of chemical rotation is both times consuming and expensive, since the applicators must have at minimum three different chemical compounds for various types of insect pests.

Most chemical insecticides must be used and applied with extreme caution. Typically, the applicator must at all times wear special protective personal protection clothing. This includes the use of respirator and eye protection, as sell as chemical impervious coveralls and gloves. Since the insecticides produce a toxic residue and are by nature long lasting and complex compounds, over a period of time, direct exposure to insecticides can lead to human health concerns and in some cases direct exposure to certain insecticides can lead to toxic shock and death.

Due to the very nature of the insecticide that is designed to leave behind a toxic residue on either plant surfaces or in the soil, environmental damage is a direct concern. There has been increasing concern about the impact of groundwater by complex pesticide compounds that do not break down into innocuous substances. It has been documented that pesticide compounds have directly impacted groundwater aquifers and directly threated environmental security.

In addition to concerns about groundwater impacts, insecticides often impact non-target organisms within the environment that come into contact with the insecticide. These organisms include fish, birds, other non-pest insects, and all forms of animal life. There have been hundreds of documented cases of insecticides such as DDT and others entering the food chain and impacting birds such as the American bald eagle, storks, rainbow trout and others.

Because of the problems associated with the use of traditional chemical insecticides a need exisits for a safe method to control insect pests commonly found in commerical horticulture and agriculture.

An object of the present invention is to provide a safe method of controlling insect populations through either direct killing or by killing of insect larvae and food sources It is an another object of the present invention to provide a method to control insect populations that is safe and convenient to use.

It is another object of the present invention to provide a method of controlling insect pests, which reduces worker exposure to hazardous and toxic compounds.

It is yet another object of the present invention to provide a method of protecting plants from insect infestations through the entire life cycle of the plant.

SUMMARY OF THE INVENTION

It has now been found that these and other objects of the invention may be attained in a method for control of insects which includes applying a solution of hydrogen peroxide to plant tissue, said hydrogen peroxide being a solution having a concentration of between 0.05 to 3.00%.

In some cases the hydrogen peroxide solution has a concentration of between 0.05 and 1.5%. Some forms of the invention may utilize a hydrogen peroxide solution that further includes an acid selected from the group consisting of acetic acid and phosphoric acid.

In some cases the hydrogen peroxide solution is applied to the plant tissue at a variety of stages in the plant production cycle. Other application of the invention include applying misting the hydrogen peroxide solution over terminal stem cuttings until they reach root sufficiency.

DESCRIPTION OF THE PREFERRED EMBODIMENT

The method in accordance with the invention utilizes hydrogen peroxide, sometimes known as peroxygen, for the purpose of killing the most common plant pathogens in greenhouses, lawns, gardens, orchards, forests, and other agricultural crops. It was discovered that when a dilute solution of hydrogen peroxide is applied to living plants by spray, mist, fog or immersion (including the root system), the plant pathogens present on the surfaces were either totally eradicated or substantially reduced. The plants suffered no adverse affects from the treatment. Daily treatments with hydrogen peroxide had no adverse effect upon the health of the plants. There were no signs of discoloration of the flowers on ornamental plants. The most obvious effect was the elimination of the fungi, particularly on the plant leaves and stems since fungi are extremely visible on these areas. The effect of the hydrogen peroxide upon pathogenic bacteria and viruses were not observed since these diseases are relatively uncommon. However, the effects of hydrogen peroxide upon bacteria and viruses has been well documented in the literature and one could expect the same sanitizing effect upon these agents as was observed upon the more resistant fungal agents. The important point to remember is that hydrogen peroxide is a very powerful disinfectant and yet does not harm delicate plant tissues when used at a concentration lethal to the plant pathogens. Other added advantages of hydrogen peroxide disinfection are, the lack of a residue upon the treated surfaces, and the totally innocuous breakdown products of water and oxygen which are readily absorbed by the plants.

Still another surprising advantage of the application of even the moderate concentration of hydrogen peroxide that will not harm delicate plant tissue is that this moderate concentration will substantially reduce the population of insects in the plant environment. Since insects are a source of plant diseases and even the presence of insects on plants make the plant unsuitable for sale. Plants having an infestation of insects are even worse than being unsuitable for sale in that if any such plants were to reach any retail or wholesale customer for such plants it is unlikely that the customer will quickly purchase any additional plants from the same supplier.

The invention may usually be attained in a method in which a hydrogen peroxide solution of between 0.05% and 3.0% is applied periodically to the plant material throughout the plant production cycle. The method permits the hydrogen peroxide solution to be applied to the plant material continuously and or periodically during this time period without adversely affecting the plant growth.

More particularly, a solution of hydrogen peroxide diluted with water to a total hydrogen peroxide concentration of about 0.05 to 3.00 percent is preferred. A solution of about 1.0% hydrogen peroxide is preferred for initial application to plant tissue already infected with microorganism while a solution of about 0.05% is preferred for repeated applications intended to protect plant tissue from microbial infection. The addition of acetic or phosphoric acid to the solution at a concentration of about 0.05% is useful to stabilize the hydrogen peroxide solution in certain water conditions. Any commercial source of hydrogen peroxide solution may be used to carry out the method of the present invention. Typical concentrations commercially available are between 3 and 70 percent hydrogen peroxide. While any of these forms will work in the present invention, it may be more convenient in some cases to purchase a 50% concentration and then dilute that solution down to the appropriate concentration in accordance with the present invention. One method which may be useful for diluting concentrated solutions is to use a Dosatron™ Proportioner made by Dosatron International, Inc.

The solution may be delivered to the plant tissue by standard pesticide application techniques. High volumes may be applied by hydraulic spraying and low volumes may be applied by misting or fogging. The solution may also be applied by injecting the hydrogen peroxide into a commercial cooling system. Alternatively, the hydrogen peroxide may be injected into a recirculating subirrigation nutrient system solution to control microbial growth in the irrigation water.

The hydrogen peroxide solution may be applied to the plant tissue at a variety of stages in the plant production cycle. This is illustrated by ever present problem of *Botrytis cinerea foliar* and stem blight experienced in all zonal geranium propagation. By injecting hydrogen peroxide solution into the water that is misted over the terminal stem cuttings until they reach root sufficiency surface microbial contaminants, including most notably Botrytis, will be reduced. This will dramatically reduce the cost of propagating this crop by reducing plant mortality, plant handling and fungicide applications.

Another unexpected result of the field trials with the hydrogen peroxide product was the lethal effect it had upon the insect pest that were present in the greenhouse. The insect pests that were adversely affected by the peroxide treatment were, mealy bug, aphids, spider mites, white fly, fungus gnats, and thrip. The effects of the hydrogen peroxide appear to be upon the embryonic stages of the insects except for fungus gnats which disappeared probably because of the removal of the fungus in the greenhouse which is their source of food. Because of the short life time of most insects and the vulnerability of insects in the embryonic stages the treatment is highly effective.

The use of the method in accordance with the present invention is illustrated by the following examples:

EXAMPLE #1

The effectiveness of hydrogen peroxide in reducing the activity of Botrytis cinerea on the surface of zonal geranium cuttings during mist propagation can be seen by referring to Table 1. In this study 500 zonal geranium cuttings were treated with a mist during the entire course of their propagation. One mature leaf from each of 10 terminal stem cuttings following treatment were sampled and the data was averaged.

TABLE 1

|  | TREATMENT | MICRO-ORGANISMS/LEAF |
|---|---|---|
| Control Group | 100% Water | 38,679 |
| Hydrogen Peroxide | 0.05% Hydrogen Peroxide | 38 |

The present invention contemplates the use of the method in accordance with the present invention on any type of plant material and virtually any known method of application of a such solution. The limitations to be considered are (1) the concentration must not be so great as to cause burning of the plant tissue and (2) the equipment used for application must have all parts of the application equipment in contact with the solution be constructed of materials that are compatible with the solution.

EXAMPLE #2

Roses in four different greenhouses were each sprayed at least four times with a 1 % Hydrogen Peroxide solution. To insure objectivity, the greenhouses selected were not all commonly owned and many varieties of roses were included in the testing. The applications killed or seriously reduced the total mold count, including Botrytis and those molds causing Powdery Mildew. The effectiveness of the spray was measured by microbial culture of the surfaces of the greenhouse and the leaf surfaces of the treated and untreated plants. After the first application of the 1 % hydrogen peroxide mixture the treated plants and surfaces were almost 100% free of total fungi as measured by the microbial culture methods. It is well known that these fungi are airborne. Thus, without further corrective action re-contamination of the environment is expected. Subsequent daily applications of a 500 PPM (parts per million) hydrogen peroxide mixture were made over the course of several weeks. During that time no recontamination by fungi occurred as determined by the microbial culture method. No adverse effects were noted upon the plants after six weeks of observation.

EXAMPLE #2

The treatment of the greenhouses in Example # 1 resulted in the destruction of the larval stages of the mealy bug, white fly, aphids, spider mites, and thrip. Also eliminated, were fungus gnats, probably due to the removal of their food source.

EXAMPLE #3

Hydrogen peroxide was introduced into the cut flower water solution at the rate of 500 PPM to keep the flowers fresh after harvest. A comparison was made with the various commercial products available for this purpose. Drooping of the necks, clarity of the water, color of the flowers, and general all-over appearances were observed for a period of two weeks. Additional water was added to all containers as needed. The hydrogen peroxide containers remained clear through the period and all flowers remained in excellent condition with only slight neck droop observed. The commercial products were about 50–75% as effective as the hydrogen peroxide.

EXAMPLE #4

A dilute solution of hydrogen peroxide was introduced into the misting system used on a rooting bench where cuttings of plants are placed in rooting medium and kept moist until roots are produced. Prior to sticking the cuttings in the rooting medium the cutting were dipped in 0.5% hydrogen peroxide. This procedure virtually eliminated cutting loss due to root rot and other infectious pathogens that can claim up to 50% of untreated cuttings

EXAMPLE #5

In the cut flower industry, the moist flowers are wrapped in plastic prior to placement in the shipping boxes for transit. Ice is added to the boxes in many cases to help keep the flowers fresh during transit. This closed, moist environment is very conducive to Botrytis and Black Spot Mold. Wetting the flowers with a dilute solution of hydrogen peroxide prevented and or delayed the appearance of the detrimental fungi. The addition of hydrogen peroxide to the water supply producing the ice also insured a slow release of hydrogen peroxide throughout the transit time.

EXAMPLE #6

The wooden boxes used for the transportation of cut roses can be a source of contamination. Chemical disinfection of the wooden boxes is difficult due to the porous nature of the wood. Chemical disinfectants are prone to leaving a residual in the wood which can be harmful the fragile flowers. Sanitizing with a 1% solution of hydrogen peroxide proved very effective, leaving no residue and aiding in the removal of many stains due the reuse of the boxes.

It will be further understood that the example #3 referred to above that relates to cut flowers is representative of a still broader application of the present invention. More specifically, immersion of fruit such as peaches into a hydrogen peroxide solution will control both bacteria and fungi on the fruit and Will thus dramatically increase shelf life. Advantageously, the hydrogen peroxide breaks down into hydrogen and oxygen and leaves no residue on the produce. The implications of this aspect of the invention are as dramatic for (1) cultivation of food products and preservation of food products and cuttings of food product plants as it is for (2) cultivation of ornamental plants and preservation of ornamental plant cuttings. It will be understood that the term "plant tissue" as used herein is intended to include plants produced for food, the fruit of such plants, plants produced for ornamental purposes and the cuttings of both ornamental plants and plants produced for food.

The disclosed method achieves four of the five principles of control by a single procedure. Resistance by genetic mutation is not affected since no evidence was developed that hydrogen peroxide is a mutagen.

INSECTICIDE PROPERTIES

In the course of testing the capabilities of the process of the invention for efficacy in decontamination of greenhouses and crops of pathogenic bacteria, fungi, viruses and problematic algae an additional benefit was suggested. More specifically, it was suggested that the process would reduce the insect populations in addition to reducing the microbial populations.

In order to further investigate this effect, a commercial greenhouse, 96 ft. Long and 25 ft. Wide, was filled with various species of household plants, of which most had infestations of some type of insect pest. (Table 2) All other treatments were stopped two weeks prior to treatment with the solution of the present invention. Yellow sticky cards were placed throughout the greenhouse for three days prior to treatment and then were counted for the various species of insects present. The greenhouse was then treated with 12 gallons of a 1:50 dilution of the solution of the present invention using a Dram™ hydraulic sprayer. The house was sprayed on three day intervals for a period of three weeks. Sticky cards were placed in selected areas through out the greenhouse during the three week period.

RESULTS

The insect counts of the pre-treatment cards indicated infestation that was almost too numerous to count. The typical insects present are tabulated. (Table 3) Thrips were the most numerous. As indicated in Table 3, a 72 hr. Exposure of the sticky cards did not indicate any significant reduction in insect populations after one treatment with the solution of the present invention. However, 10 days and post 5 treatments, the sticky cards demonstrated a marked reduction of insect populations as indicated by the low counts of Whitefly, Aphid, Fungus Gnats and others. Thrips was also greatly reduced considering the fact that the sticky cards were exposed for a seven day period.

Subsequent treatments have further reduced the insect populations (indicated by the fresh sticky cards) to the extent that only an average of 7–10 Thrips were present after a 72 hour exposure time. See Tables 4 and 5.

It must be noted, throughout the treatment period, there was no evidence of phytotoxicity or any other detrimental affect to the plants, most of which were in bloom. There was however, a great deal of foaming of the the solution of the present invention on the leaves of the New Guinea Impatiens, which had been heavily infested by aphids. The foaming was due to the black mold growing on the excrement of the aphids, and the solution of the present invention quickly neutralized the mold.

CONCLUSION

A preventative application of the solution of the present invention on a weekly basis, with three applications per week, either by hand or done automatically with low volume foggers can not only reduce the presence of pathogenic fungi, bacteria and virus from within the greenhouse environment, but it appears there is promise for the control of many insect pests at the same time.

TABLE 2

PLANT AND INFESTATION TYPES

| PLANT VARIETY | INSECT TYPE |
| --- | --- |
| Citrus | Mealy Bug |
| Dahlia (In Flower) | Thrips, Aphids, White Fly |
| Super Zinnias | Thrips |
| Margarita Daisy (in Flower) | Thrips |
| Geraniums (In Flower) | No Insect Infestation |
| Vinca | Thrips, Aphids, White Fly, Fungus Gnats |
| Mandavilla | No Insect Infestation |
| Morning Glory | No Insect Infestation |
| Ferns | No Insect Infestation |
| Jades | No Insect Infestation |
| Various Ivy | No Insect Infestation |
| New Guinea Impatiens (In Flower) | Thrips |

TABLE 3

PRE TREATMENT (72 HOUR CARD EXPOSURE)

| CARD | THRIPS | WHITE FLY | APHID | FUNGUS GNAT | OTHER | TOTAL |
| --- | --- | --- | --- | --- | --- | --- |
| 1 | 484 | 69 | 101 | 15 | 16 | 283 |
| 2 | 183 | 32 | 15 | 17 | 11 | 258 |
| 3 | 274 | 358 | 17 | 15 | 3 | 667 |
| 4 | 183 | 49 | 31 | 10 | 47 | 320 |
| 5 | 741 | 277 | 37 | 8 | 1 | 1064 |

TABLE 4

72 HOUR POST ONE TREATMENT

| CARD | THRIPS | WHITE FLY | APHID | FUNGUS GNAT | OTHER | TOTAL |
| --- | --- | --- | --- | --- | --- | --- |
| 1 | 320 | 85 | 88 | 2 | 12 | 507 |
| 2 | 220 | 65 | 4 | 3 | 9 | 301 |
| 3 | 350 | 270 | 2 | 0 | 35 | 657 |
| 4 | 85 | 84 | 64 | 0 | 25 | 258 |
| 5 | 430 | 350 | 46 | 0 | 0 | 826 |

TABLE 5

10 DAYS POST FIVE TREATMENT WITH A ONE WEEK CARD EXPOSURE

| CARD | THRIPS | WHITE FLY | APHID | FUNGUS GNAT | OTHER | TOTAL |
| --- | --- | --- | --- | --- | --- | --- |
| 1 | 14 | 0 | 0 | 0 | 2 | 16 |
| 2 | 35 | 0 | 0 | 0 | 1 | 36 |
| 3 | 16 | 0 | 0 | 0 | 0 | 16 |
| 4 | 35 | 0 | 0 | 0 | 0 | 35 |
| 5 | 72 | 0 | 0 | 0 | 12 | 84 |

The invention has been described with reference to its illustrated preferred embodiment. Persons skilled in the art of such devices may upon exposure to the teachings herein, conceive other variations. Such variations are deemed to be encompassed by the disclosure, the invention being delimited only by the following claims.

Having thus described my invention we claim:

1. A method of killing insects on plant tissue which comprises:

applying a solution that includes hydrogen peroxide to plant tissue, said hydrogen peroxide in the solution having a concentration of between 0.05 to 3.00% by weight.

2. The method as described in claim 1 wherein: the hydrogen peroxide in the solution has a concentration of between 0.05 and 1.5% by weight.

3. The method as described in claim 2 wherein:

the method further includes at least one step of reapplying the solution.

4. A method for killing insects on plant tissue which comprises: applying a solution that includes hydrogen peroxide to plant tissue, said hydrogen peroxide in the solution has a concentration of between 0.05 and 1.5% by weight and the solution further includes an acid selected from the group consisting of acetic acid and phosphoric acid.

5. The method as described in claim 4 wherein:

the solution is applied by hydraulic spraying.

6. The method as described in claim 4 wherein:

the solution is applied by misting.

7. The method as described in claim 4 wherein:

the solution is applied by fogging.

8. The method as described in claim 4 wherein:

the solution is applied by injecting the hydrogen peroxide into a commercial cooling system.

9. The method as described in claim 4 wherein:

the solution is injected into a recirculating subirrigation nutrient system solution to control microbial growth in the irrigation water.

10. The method as described in claim 4 wherein:

the solution is applied to the plant tissue at a variety of stages in the plant production cycle.

11. The method as described in claim 4 wherein:

the solution is injected into the water that is misted over terminal stem cuttings until they reach root sufficiency.

12. The method as described in claim 4 wherein:

the step of applying said solution to plant tissue is repeated a plurality of times.

13. The method as described in claim 4, wherein:

the method further includes at least one step of reapplying the solution.

14. The method as described in claim 5 wherein:

the method further includes at least one step of reapplying the solution.

15. The method as described in claim 6 wherein:

the method further includes at least one step of reapplying the solution.

16. The method as described in claim 7 wherein:

the method further includes at least one step of reapplying the solution.

17. The method as described in claims 8 wherein:

the method further includes at least one step of reapplying solution.

18. The method as described in claim 9 wherein:

the method further includes at least one step of reapplying the solution.

19. The method as described in claim 10 wherein:

the method further includes at least one step of reapplying the solution.

20. The method as described in claim 11 wherein:

the method further includes at least one step of reapplying the solution.

* * * * *